United States Patent
Webster

Patent Number: 6,143,431
Date of Patent: Nov. 7, 2000

[54] PRODUCTION OF PALLADIUM-103

[76] Inventor: Brian A. Webster, 957 Lillian Street, Coquitlam, British Columbia, Canada

[21] Appl. No.: 09/072,077

[22] Filed: May 4, 1998

[51] Int. Cl.[7] .............................. B32B 15/01; C25D 3/50; C25D 5/24; G21G 1/10

[52] U.S. Cl. .......................... 428/669; 205/265; 376/158; 376/195; 376/201; 424/1.11; 424/646; 427/5; 428/670; 600/3; 600/8

[58] Field of Search .................................... 428/669, 670; 600/3, 8; 376/158, 195, 201; 427/5; 424/1.11, 646; 205/265

[56] References Cited

U.S. PATENT DOCUMENTS

| | | | |
|---|---|---|---|
| 3,351,049 | 11/1967 | Lawrence | 600/8 |
| 4,702,228 | 10/1987 | Russell, Jr. et al. | 600/8 |
| 4,815,449 | 3/1989 | Horowitz | 600/8 |
| 4,994,013 | 2/1991 | Suthanthiran et al. | 600/8 |
| 5,163,896 | 11/1992 | Suthanthiran et al. | 600/8 |
| 5,178,745 | 1/1993 | Abys et al. | 205/265 |
| 5,405,309 | 4/1995 | Carden, Jr. | 600/8 |
| 5,575,749 | 11/1996 | Liprie | 600/3 |

OTHER PUBLICATIONS

Ames et al. (1960), "Spins and Decay Modes of Certain Neutron–Deficient Silver Isotopes," *Phys. Rev.* 118(6):1599–1604; Jun. 1960.

Harper et al. (1961), "The Thick Target Yield and Excitation Function for the Reaction $Rh^{103}$ $(pn)Pd^{103}$," Oak Ridge National Laboratory Report, Central Files Number 61–5–67; May 1961.

White et al. (1962), "Isometric States of $Ag^{103}$, $In^{116}$, and $Sb^{114}$," *Can J. Phys.* 40:865–878; Dec. 1962.

Bibijana Cujec (1963), "Nuclear Structure Studies in the Palladium Isotopes with (d,p) and (d,t) Reactions," *Phys. Rev.* 131(2):735–744; Jul. 1963.

Ove T. Hogdahl (1961), "The Radiochemistry of Palladium," Natl. Acad. Sci.—Natl. Res. Council. Publication NAS–NS 3052; Dec. 1961.

Shiban–Eldin et al. *Table of Isotopes*, 7th ed., U.S. Dept. of Energy; No Date.

Firestone et al. *Table of Isotopes*, 8th ed., U.S. Dept. of Energy; No Date.

Scholten et al. (1980), "Neutron Pickup Reactions on the Even Palladium Isoptopes and the Deeply Bound Hole–State Excitation," *Nucl. Phys.* A348:301–320; Dec. 1980.

*Primary Examiner*—Deborah Jones
*Assistant Examiner*—Robert R. Koehler
*Attorney, Agent, or Firm*—Testa, Hurwitz & Thibeault, LLP

[57] ABSTRACT

Palladium-103 radiochemical of high radionuclidic purity can be produced in commercial scale quantities by irradiating enriched Palladium targets comprising a mixture of Pd isotopes with protons or deuterons in the 10–50 MeV energy range. Commercially viable batch sizes with acceptable specific activity of the product Pd-103 are achieved by adjusting the irradiation energy, irradiation time, irradiation current, current density, plated target mass, plated target shape, plated target size, target isotope enrichment levels, and incident angle of the target to the beam. The method for the production of Pd-103 comprises providing a target material enriched with Pd isotopes comprising atomic masses equal to or greater than Pd-103, applying the target material onto a target support; irradiating the target material with protons or deuterons of sufficient incident energy and time to convert at least some of the Pd isotopes within the target material to Pd-103; and purifying Pd from the non-Pd components.

24 Claims, 6 Drawing Sheets

PRODUCTION OF PALLADIUM-103

The present invention relates to the preparation of palladium-103 (Pd-103). More specifically, it relates to a method for the production of Pd-103 using proton bombardment using targets enriched with palladium isotopes.

BACKGROUND OF THE INVENTION

Palladium-103 (Pd-103) has a half-life of 16.97 days. It has many desirable properties for use as a therapeutic agent and is used, for example, in the treatment of cancers, such as prostate cancer. Its use with such seeds has been suggested as an alternative to I-125 (U.S. Pat. No. 3,351,049; U.S. Pat. No. 4,702,228; U.S. Pat. No. 5,405,309). In such applications, Pd-103 coated substrates, are subsequently coated or encapsulated by an inert material, and are used to produce small seeds, which are implanted directly into a tumour in order to provide irradiation for therapeutic treatment and inhibition of tumour growth.

The current production of Pd-103 involves neutron bombardment of a Pd-102 enriched (from about 50 to about 80%) substrate (U.S. Pat. No. 4,702,228), which is incorporated by reference), or transmutation of rhodium-103 by proton bombardment (U.S. Pat. No. 5,405,309; Harper et al 1961 both of which are incorporated by reference). The preparation of Pd-103 via transmutation of enriched Pd-102 target material is known to result in relatively low yields since only a small portion of the Pd-102 target is converted (U.S. Pat. No. 4,702,228; Harper 1961). The conditions for this reaction requires the use of a reactor to bombard the target material for 21 days, at a neutron flux of $4 \times 10^{14}$ n/cm²/s in order to provide an acceptable specific activity of Pd-103 (U.S. Pat. No. 4,702,228). U.S. Pat. No. 5,405,309, highlights other problems associated with producing Pd-103 from the transmutation of Pd-102 target materials which include:

the requirement for the use of high flux reactors;
long exposure times of the target to the neutron beam;
heterogeneous target materials comprising from 20–50% of other materials, including other Pd and non-Pd-isotopes, and therefore the product is of low specific activity;
low radionuclidic purity;
due to the combination of these above factors, a lack of predictability of the specific activity of the final product;
the high cost of the Pd-102 starting material; and
the low availability of Pd-102 starting material.

It is accepted within the art that methods that use bombardment involving (n,γ) reactions (i.e. Pd-102 to Pd-103) are problematic due to quality issues associated with the final product. Pd-103 produced by this method is contaminated with impurities arising from other isotopes that are produced during the bombardment process. Furthermore, the use of Pd-102 for ion bombardment is also limited due to the high cost of Pd-102.

Second generation production of Pd-103 involves the use of Rhodium 103 targets, bombarded with cyclotron-produced protons at 10–17 MeV (U.S. Pat. No. 5,405,309; Harper et al 1961). This method suffers the following issues:

difficulty of manufacturing robust Rhodium targets;
dissolution resistance of Rhodium metal; and
low production rates.

Other target materials used to produce Pd include high energy irradiation of silver (White et al 1962) or enriched Cadmium-106 materials. However these methods have limitations in their commercial application. For example the irradiation of silver is problematic since a non-compact cyclotron with high energy (70 to 90 MeV) is required. Also, Pd-100 is produced in this reaction which is undesirable, as Pd-100 decays to Rh-100 producing high γ emission. Furthermore, target yields are limited since typical cyclotron beam currents of 100 μA are used, and large amount of other isotopes are also formed resulting in subsequent radioactive waste issues of non-target isotope products. Irradiation of enriched Cadmium-106 is also problematic since a high energy (40 to 50 MeV) cyclotron is required, with target yields limited due to a 250 μA beam current within the cyclotron. Furthermore, this method results in a low predicted makerate, and high cost and low availability of Cd-106.

Several reports have analysed inter-isotope conversions of Pd using (d,t) reactions. For example, Scholten et al (1980) examines reactions of Pd-102, 104,106,108 and 110 using deuteron beams of 50 MeV, or ³He at 70 MeV. Similarly, Cujec (1963) discloses the bombardment of the even numbered isotopes of Pd (Pd-104,106 and 108) using 15 MeV deuterons and an analysis of the Pd-104(d,t)Pd-103 reaction. Furthermore, Ames et al (1960) disclose reactions of Pd-102,104,106 and 108 bombarded with 11 MeV, below the (p,2n) threshold for Ag-103 production, and characterize the production of Ag-104. Ames et al also characterize the production of Ag-103 from Pd-104 with protons of 18.5 MeV energy (i.e. at the lower limit of the reaction) and the Pd104(p,2n)Ag103 reaction. Products produced within the above studies include Pd-103, however, no mention of product material recovery, optimizing make-rates of Pd-103, or providing for a commercially viable method for the production of Pd-103 is disclosed.

Another limitation in the above prior art methods for the production of Pd-103 products is related to difficulties in the separation of the product from the target support that is used for the products preparation. However, a method for optimizing the separation of target material from the target support is provided for by the method of this invention.

This invention is directed to a novel method for the production of Pd-103 that over comes the deficiencies of prior art methods. The method of this invention uses existing, commercially available, high capacity compact cyclotrons which are in common use for isotope production, it uses more cost effective, commercially available target materials compared to prior art methods, for example the method involving Pd-102. For example, the cost of enriched Pd-102 as a starting material is several fold that of a suitable enriched Pd-104 target. Furthermore, the production of Pd103 from Pd-104 should comprise as little Pd-102 as possible. The use of Pd-102 as a starting material, for cyclotron irradiation, is undesired since during irradiation both Pd-101 and Pd-100 are produced. These Pd isotopes decay to Rh-101 and Rh-100, and while Rh-101 is innocuous, Rh-100 is characterized problematic due to its γ ray spectrum. Therefore, this invention also helps reduce the amount of Pd-101 and Pd-100 that is synthesised using associated prior art methods. Furthermore, the method of this invention uses a simple and effective chemical process for the complete recovery of the Pd-103, and produces large batches of Pd-103 of high radionuclidic purity and of acceptable specific activity. As a result, the method of this invention provides for the commercially feasible production of Pd-103.

SUMMARY OF THE INVENTION

The present invention relates to the preparation of palladium-103.

According to the present invention there is provided a method for the production of Pd-103 comprising;
 i) providing a target material enriched with Pd isotopes comprising atomic masses equal to or greater than Pd-103;
 ii) applying the target material onto a target support;
 iii) irradiating the target material with protons or deuterons of sufficient incident energy and time to convert at least some of the Pd isotopes within the target material to Pd-103; and
 iv) purifying Pd from non-Pd components.

Furthermore, this invention is directed to the above method wherein the target material is enriched with Pd-104, Pd-105, Pd-106, or a combination thereof. Preferably, the target material is enriched with Pd-104.

This invention also relates to a method as described above wherein the target material is applied to a target support as a foil, or using electroplating, deposition, or precipitation, preferably, the target material is applied using electroplating. Also considered within the scope of the present invention is the method as described above, wherein the target material is formed by layering Pd isotope-containing target materials so that each layer is enriched with Pd isotopes comprised of predominantly a different atomic mass.

This invention also relates to the method as described above wherein the target support is protected by a coating comprising a barrier layer. Preferably the barrier layer is comprised of rhodium.

Also included within the method as described above, is a method wherein the incident energy of said protons or deuterons in step iii) is greater than about 15 MeV. Furthermore, this invention includes a method wherein the protons or deuterons of step iii) are provided as a beam, angled from about 1 to about 90° as measured from the surface of the target material. Preferably, the incident energy of the protons or deuterons is from about 23 to about 30 MeV, and the angle of the proton or deuteron beam is about 7° as measured from the surface of the target material.

This invention is also directed to the method as described above wherein the target material is of a shape that is similar to the shape of the proton beam that strikes the surface of the target material.

This invention also relates to the method as described above, wherein the target material is irradiated with protons or deuterons from about 1 hour to about 1,000 hours, and wherein the specific activity of the Pd-103 is greater than about 5 Ci/gm.

Also included within the scope of the present invention is the method as described above wherein the step of purifying Pd-103, step iv), comprises:
 i) adding a solvent to remove the target material from the target support to produce a target material solution;
 ii) adding at least one carrier, and precipitating the carrier from the target material solution;
 iii) removing the at least one carrier from the target material solution;
 v) reducing the Pd to the metallic state; and
 vi) collecting the Pd.

Furthermore, this invention includes the method as described above, wherein the step of removing the at least one carrier from the Pd, selectively removes impurities produced during the production of Pd-103. Preferably, the carrier is silver, and an iodide salt is added to selectively remove silver. However, the carrier may also be rhodium, and it is removed from the target material solution using an ion-exchange resin, or the carrier may be a combination of both silver and rhodium This invention is also directed to Pd-103 produced by the above method. Furthermore, this invention relates to a medical device coated with the Pd-103 produced by the above method.

This invention also relates to methods of coating a silver device by emersion plating wherein the silver device is immersed in an acidified Pd solution, the Pd solution containing the silver device is heated to produce a Pd-coated device, the Pd solution is removed, and the Pd-coated device is dried. In preferred embodiments of this method, the Pd solution is a 0.1 to 1.0 N HCl Pd solution. In another aspect, the present invention provides Pd-coated silver devices produced by these methods.

This invention is directed to a novel method for the production of Pd-103 that over comes deficiencies within prior art methods. The method of this invention uses existing, commercially available, high capacity compact cyclotrons which are in common use for isotope production, it uses cost effective, commercially available target materials, and provides much higher make-rates than prior art methods. Furthermore, the method of this invention uses a simple and effective chemical process for the complete recovery of the Pd-103, and produces large batches of Pd-103 of high radionuclidic purity and of acceptable specific activity. Due to the high specific activity and high purity of Pd-103 that can be prepared, the amount of target material used per batch of Pd-103 can be optimized, and recycled as required, thereby permitting cost-effective production of Pd-103. The amount of Pd-103 can be provided to a customer over a period of time while still providing commercially acceptable levels of purity and specific activity. As a result, the method of this invention provides for the commercially feasible production of Pd-103.

BRIEF DESCRIPTION OF THE DRAWINGS

These and other features of the invention will become more apparent from the following description in which reference is made to the appended drawings wherein:

FIG. 1 shows the direct and indirect nuclear reactions and decay pathways leading to the formation of Pd-103 from proton irradiation of Pd-104, Pd-105 and Pd-106.

FIG. 2 shows an embodiment of an aspect of the present invention.

DESCRIPTION OF PREFERRED EMBODIMENT

The present invention relates to the preparation of Pd-103. More specifically, it relates to a method for the production of Pd-103 using target materials enriched with Pd isotopes having atomic masses greater than Pd-103.

This invention provides for the large scale, reliable, economic production of curie to hundreds of curie quantities of Pd-103 of high radionuclidic purity and reproducible and acceptable specific activity. Commercially useful batch sizes of Pd-103 are achieved by appropriately adjusting the irradiation energy, irradiation time, irradiation current, current density, plated target mass, plated target shape, plated target size, target isotope enrichment levels, and incident angle of the target to the beam.

The method of this invention utilises protons or deuterons greater than about 10 MeV, preferably from about 10 to about 50 MeV, incident energy upon a target material of natural Pd. It is to be understood that other target materials, such as isotopically enriched Pd-104, Pd-105 and Pd-106 are also effectively used with the method of this invention. Pd-103 production is achieved via direct formation of Pd-103, and via indirect formation, from the decay of directly formed Ag-103 isotopes (FIG. 1). Deuterons may also be utilised following the method of this invention upon the above target materials. The energy selected depends upon the particle used as well as the composition or isotopic purity of the target material Without wishing to be bound by theory, in FIG. 1 there is shown the direct and indirect nuclear reactions and decay pathways leading to the formation of Pd-103 from proton irradiation of Pd-104, Pd-105 and Pd-106. The bolded boxes are highlighting the relevant naturally occurring stable isotopes of Pd and their abundances, with the half-lives of unstable nuclides shown in the other boxes.

Figure 1A:
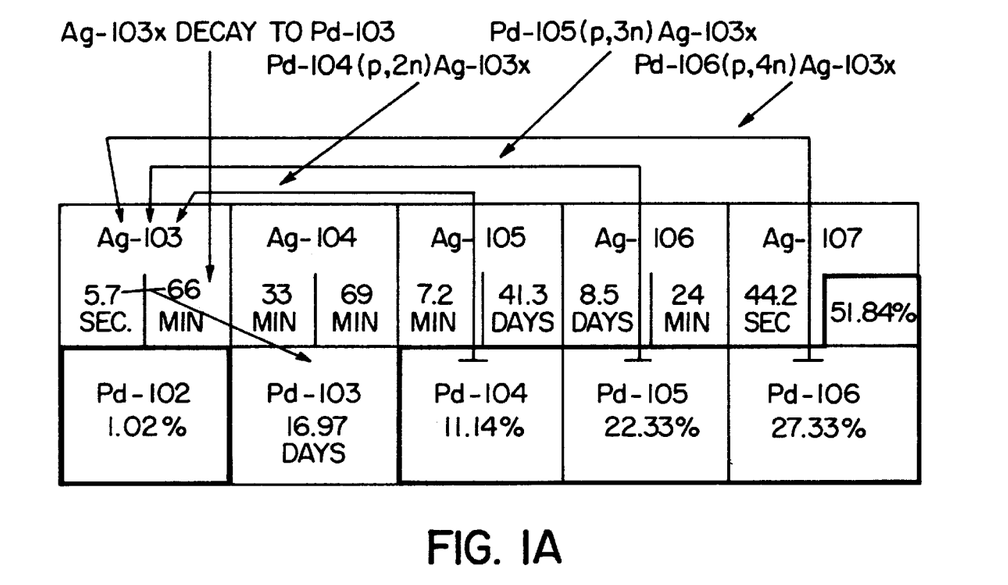
FIG. 1A shows the indirect formation of Pd-103 via a Ag-103 intermediate.

FIG. 1A identifies, via arrows, the various indirect routes that may give rise to Pd-103 from proton bombardment of Pd. These indirect routes are thought to occur from the formation of unstable Ag-103m and Ag-103 (i.e. Ag-103x) and their subsequent decay to Pd-103. Without wishing to be bound by theory, these routes may be described as reactions of the type:

proton in, x neutrons out (p, xn).

Figure 1B:
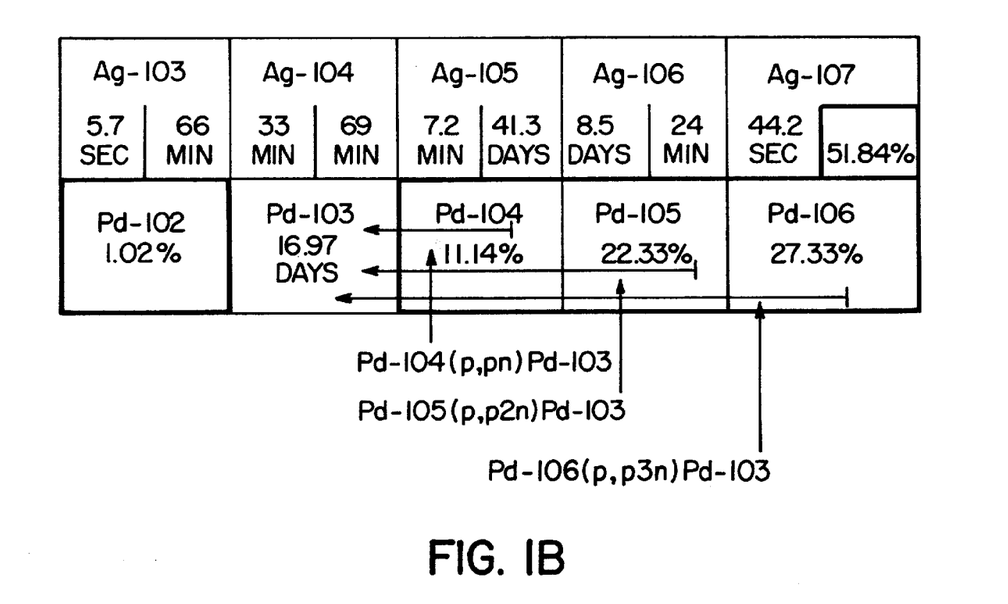
FIG. 1B shows the direct formation of Pd-103 from Pd-104,105,106.

FIG. 1B shows the relevant direct routes thought to occur leading to the formation of Pd-103 from proton irradiation of Pd-104, Pd-105 and Pd-106. Without wishing to be bound by theory, these routes may be described as reactions of the type:

proton in, proton out/x neutrons out (p, pxn).

By "substantially pure Pd-103 product" it is meant Pd-103 that comprises trace amounts of inactive and/or active rhodium and silver. Preferably the inactive rhodium and silver are at concentrations below 100 ppm, and more preferably, below 20 ppm. Preferably the active rhodium and silver are at concentrations below 0.5% of Pd-103 activity, and more preferably below 0.1%.

By "target material" it is meant the material from which Pd-103 is prepared. Target materials suitable for the preparation of Pd-103 targets following the method of this invention may be comprised of natural Pd. However, natural Pd, enriched in one or more of its isotopes of equal to or higher atomic mass than Pd-103, including Pd-104, Pd-105 and Pd-106 may also be effectively used for the production of Pd-103. Furthermore, it is to be understood that the target material may also be recycled and used within the method of this invention, and therefore, that this target material may also comprise Pd-103. In the selection of the target material it is desired to keep the amount of Pd-102 as low as possible. This is because, via similar reactions defined herein, Pd-100 (which gives rise to Rh-100) is formed from Pd-102 at proton or deutron energies desired for maximum Pd-103 production.

The composition of natural Pd is generally known to be:

| Pd-102 | 0.8–1.02% |
| Pd-104 | 9.3–11.14% |
| Pd-105 | 22.33% |
| Pd-106 | 27.33% |
| Pd-108 | 26.46% |
| Pd-110 | 11 72% |

By "specific activity" it is meant the ratio of radioactive Pd-103 to non-radioactive Pd isotopes, expressed as Ci/gm of element material.

Without wishing to limit the invention in any manner, enrichment of the Pd-104 content within natural Pd is a preferred target material. For example the target material may be enriched with Pd-104 from about 11 to about 98%. However, other suitable choices for isotopic enrichment of the natural Pd target material also include Pd-105 and Pd-106, or mixtures thereof. With an enriched Pd-104 target material of 98%, yields of Pd-103 can increase by a factor of 9 over that of natural Pd. Target materials of appropriate composition may be prepared by mixing Pd target materials of various isotopic compositions. The production make-rate may be further maximized by layering various compositions of target material within the target. For example, target materials may be layered so that Pd isotopes requiring lower energies for their conversion to Pd-103 (e.g. Pd-104), are layered first and over-layered with one or more layers of target material comprising Pd isotopes that require higher energies for conversion to Pd-103 (i.e. Pd-105, 106 etc). Therefore as the energy of the proton beam decreases through the thickness of the target material (see below), the energy level of the beam is sufficient for the conversion of the target material to Pd-103.

Figure 3:
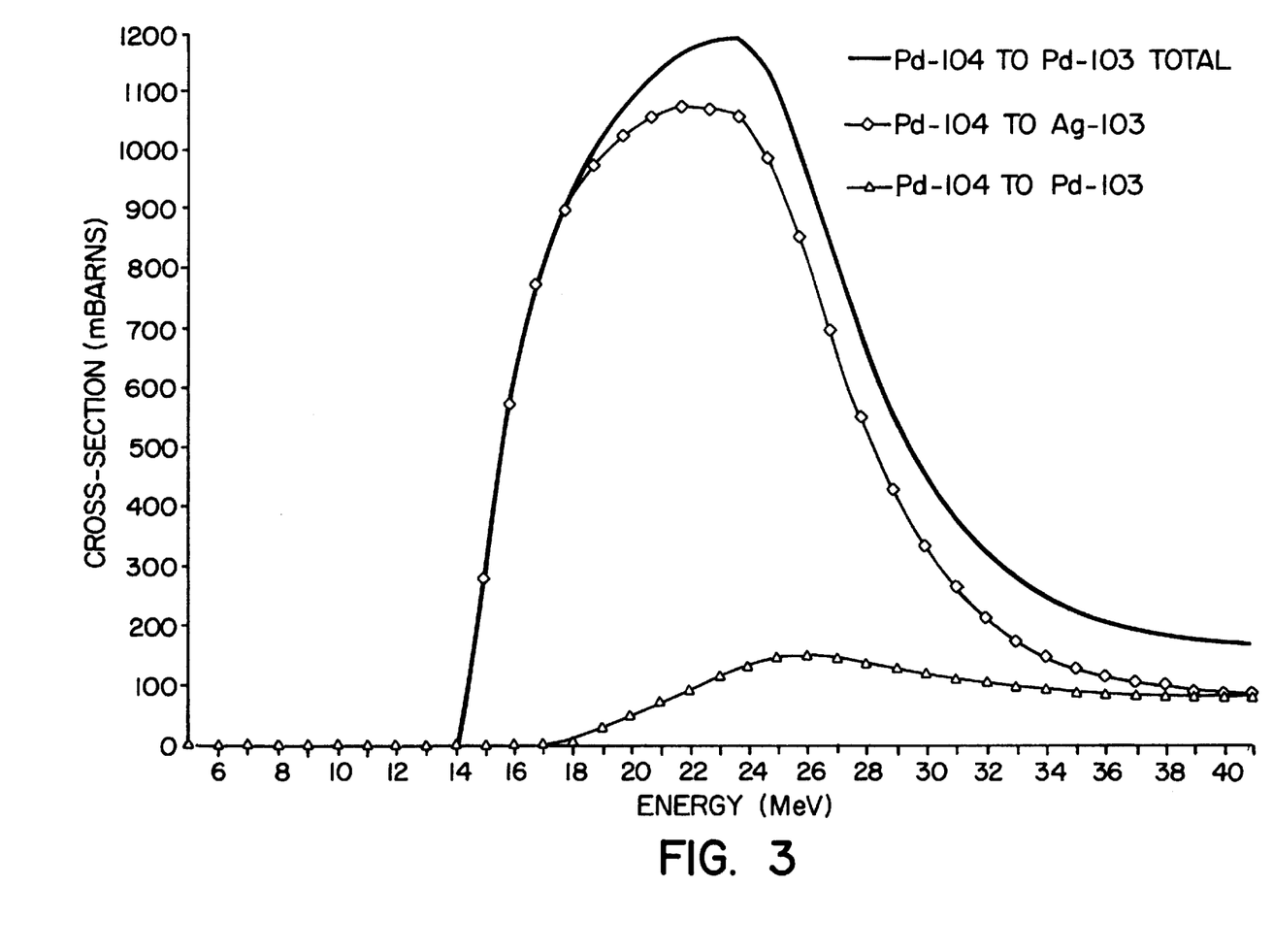
FIG. 3 is a graph showing the calculated nuclear cross-sections for the Pd-104 (p,2n) Ag-103/Ag-103m . . . Pd-103 and the Pd-104 (p,pn) Pd-103 reactions.
Figure 4:
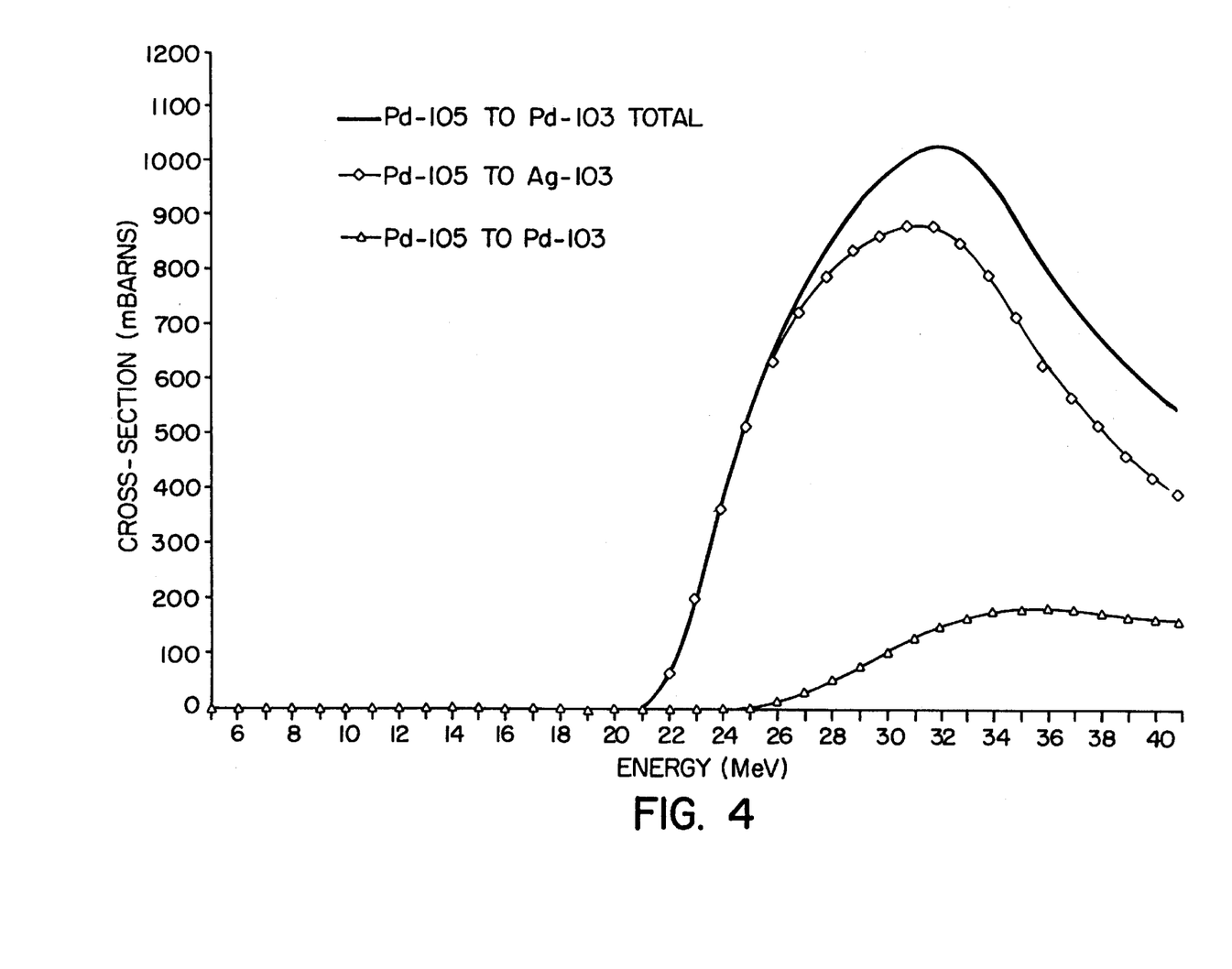
FIG. 4 is a graph showing the calculated nuclear cross-sections for the Pd-105 (p,3n) Ag-103/Ag-103m . . . Pd-103 and the Pd-105 (p,p2n) Pd-103 reactions.
Figure 5:
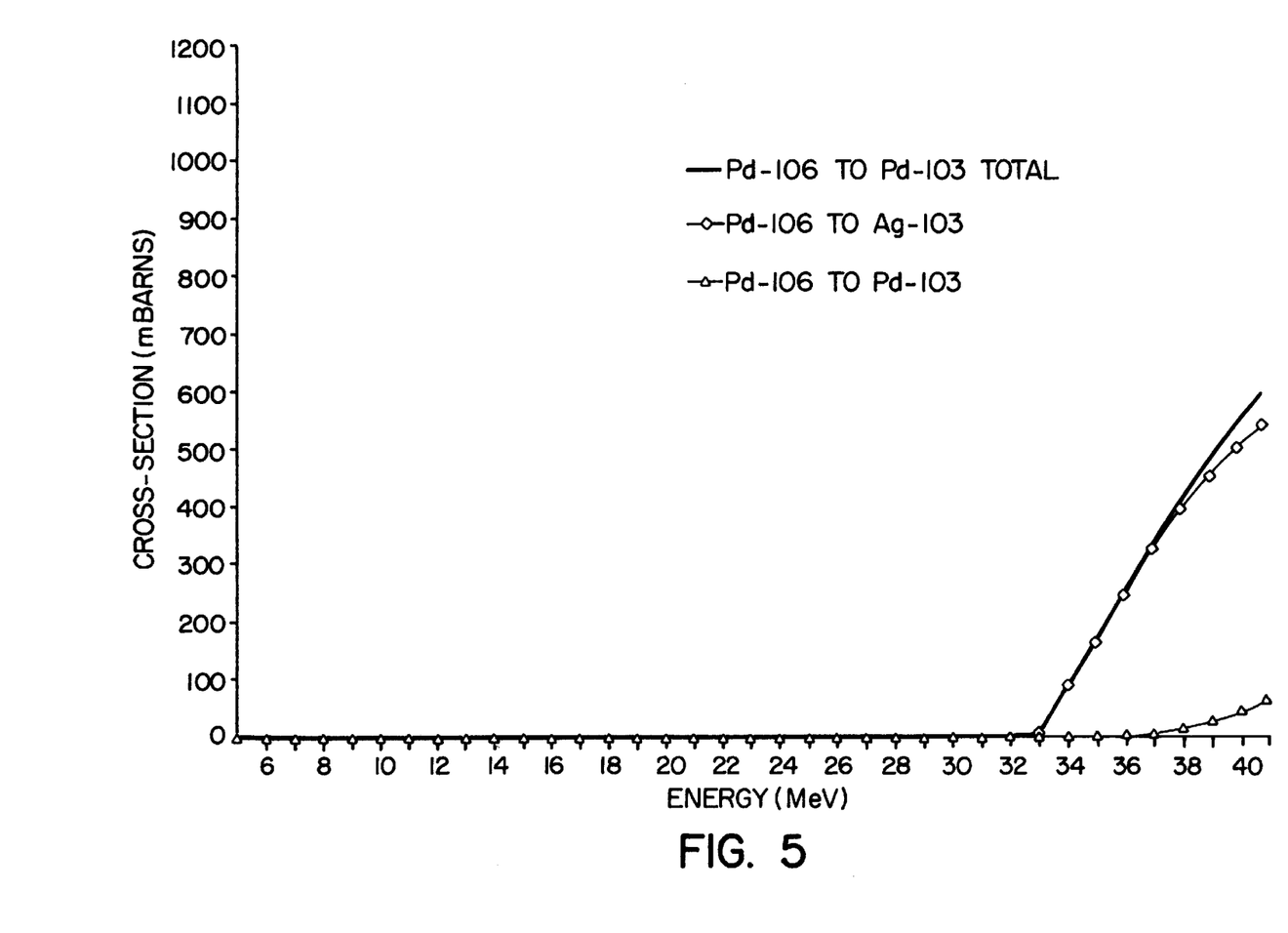
FIG. 5 is a graph showing the calculated nuclear cross-sections for the Pd-106 (p,4n) Ag-103/Ag-103m . . . Pd-103 and the Pd-106 (p,p2n) Pd-103 reactions.

There is a relationship between the composition of the target material and the energy of the proton beam required to produce Pd-103. For example, typically 24 MeV is required for a peak Pd-104 to Pd-103 reaction, while Pd-105 requires 32 MeV for the peak Pd-105 to Pd-103 reaction etc. This relationship can be determined as illustrated in FIGS. 3 to 5. FIG. 3 shows the calculated nuclear cross-sections for the Pd-104 (p,2n) Ag-103/Ag-103m . . . Pd-103 and the Pd-104 (p,pn) Pd-103 reactions; FIG. 4, the calculated nuclear cross-sections for the Pd-105 (p,3n) Ag-103/Ag-103m . . . Pd-103 and the Pd-104 (p,p2n) Pd-103 reactions; and FIG. 5 the calculated nuclear cross-sections for the Pd-106 (p,4n) Ag-103/Ag-103m . . . Pd-103 and the Pd-104 (p,p2n) Pd-103 reactions. FIGS. 3, 4 and 5 are typical of the representations of reaction yields from charged particle irradiations. The energy (MeV) of the charged particle is shown on the x axis, while the cross-section of the reaction (s) is shown on the y axis. The cross-section, in millibarns (mbarns), is the probability of the reaction(s) occurring. In all three graphs, the total probability for Pd-103 formation is shown as a bold line, and is the sum of the direct and indirect routes shown.

As an example of determining the energy requirement for a desired reaction, consider irradiation of Pd-104 as shown in FIG. 3. Assuming 100% enrichment of the Pd-104 target material, the indirect Pd-104 (p,2n) Ag-103x reaction is predicted to have a peak probability of approximately 1075 mbarns, occurring at a proton energy of 22 MeV, while the direct Pd-104 (p,pn) Pd-103 reaction is predicted to have a peak probability of approximately 150 mBarns at a proton energy of 26 MeV. The total of each of these mbarns probabilities is shown to have a peak probability of approximately 1200 mbarns at a proton energy of 24 MeV.

During irradiation of the target material, the Pd isotope absorbs and slows the proton as it passes through the target material and the proton loses energy. The amount of this energy loss/absorption is dependent on the proton's initial energy and the target material thickness (expressed as g/cm$^2$). For example, which is not to be considered limiting in any manner, if a 1.33 g, 10.2 cm$^2$ Pd-104 electroplate (0.13 g/cm2) is struck at an incident angle of 7° from the surface of the target material (therefore providing an effective target material thickness 1.07 g/cm2) with protons of 29 MeV energy, it is estimated (as calculated using proton stopping calculations) that the protons would lose an average of 14 MeV energy within the Pd-104 target material layer, and exit at an average energy of 15 MeV. From FIG. 3 we see that this energy drop, from 29 to 15 MeV, is spanning most of the probability (mbarns) for Pd-103 formation.

In the case of a product which is the same element as the target material (such as Pd-103 within a Pd-104 target), the product will not be carrier-free. The ratio of radioactive to non-radioactive atoms of the element is expressed as its specific activity (SA) as defined above. The requirement for the SA of a product is dependent on the product application and can be varied as required by adjusting the target thickness, the Pd-104 isotopic percentage (i.e. the degree of enrichment of the target material), the proton beam energy, the length of irradiation, and the number of protons in the beam per unit time (i.e. the beam current—usually expressed in $\mu$A). For example the use of Pd-103 within seeds for cancer therapy, at present requires a SA of greater than about 5 Ci Pd-103/gm Pd, and these levels are easily obtained.

Target Preparation

The Pd target material is prepared for irradiation by affixing the target Pd material to a suitable support. For example, and without wishing to be limiting in any manner, the target Pd material may be affixed onto a suitable support by electrodeposition. However, any method that results in the affixing of the target material onto the support, as would be recognized by one of skill in the art, may be used, for example, chemical deposition, precipitation, evaporation, powder deposition, metal liquid coating, salt deposition and the like. It is also to be understood that some of these coating methods may require processing prior to proton bombardment (e.g. ignition of a salt coating, reduction of a metal coating etc.). Furthermore, Pd foil may also be used for the methods as described herein.

For electrodeposition of the target material, the target support is typically made of thermally conductive material, for example, silver or copper, however, other suitable materials evident to one of skill in the art may also be employed for this purpose, for example aluminum etc. Prior to electrodeposition of the Pd target material, the target surface can be rendered more chemically inert by coating with a resistant material such as Rhodium. This more inert "barrier layer" can assist in the removal of the target material from the target during subsequent chemical processing of the target material. As would be evident to one of skill in the art, other materials that enhance this process may also be used, for example ruthenium and possibly platinum.

The mass of target material electrodeposited onto the target can vary depending upon the application and ranges from about 0.05 g to about 20 g. However, applications of target material comprising from about 0.1 g to about 5 g are preferred. The mass required for effective application of this invention may vary dependant on a range of factors including:

the quantity of Pd-103 radioactivity required;

the desired radionuclidic purity of the Pd-103 product;

the desired SA (ratio of Pd-103 to inactive Pd);

the irradiation energy of the particle applied to the target;

the angle at which the target is struck by the particle;

the physical size and thickness of the target material prepared onto the target;

the enrichment of the target material with Pd isotopes of higher atomic mass.

The shape of the target material prepared on the substrate can vary. However, it may be desired that this shape maximizes exposure of the target material to regions of medium to high incident particle current, and minimizes the exposure of target material at regions of low particle currents. The shape of the target material (e.g. see FIG. 2B) may be determined due to economic considerations and product specific activity considerations.

Figure 2A:
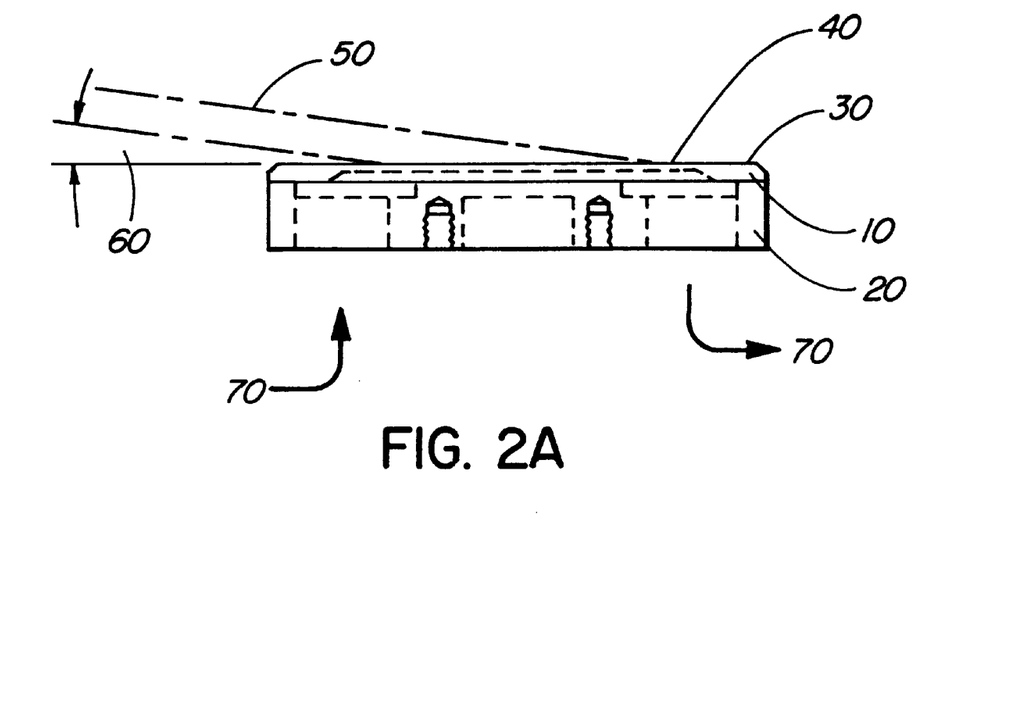
FIG. 2A shows a target coated with a protective Rhodium layer, onto which an enriched Pd-104 target material has been electroplated.
Figure 2B:
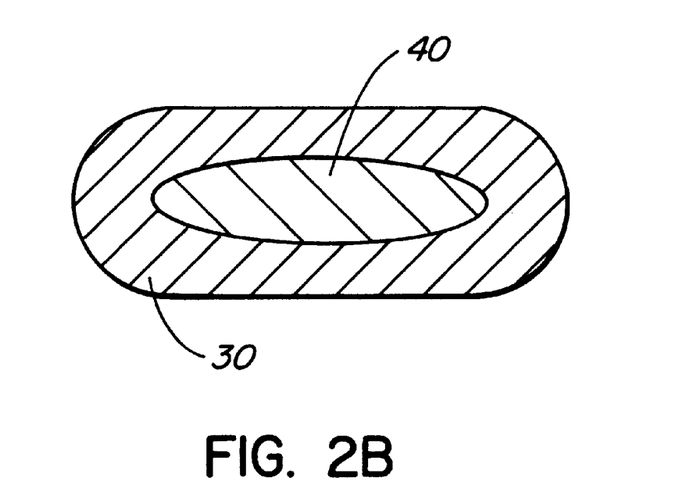
FIG. 2B shows one of many shapes the plated Pd may take in order to maximize the proton beam current while minimizing the target material required. In this example, 1.33 grams of Pd-104 was electroplated onto the Rhodium layer over an area of 10.2 cm$^2$.

An example, which is not to be considered limiting in any manner, of a target material—barrier layer—proton beam arrangement is shown in FIG. 2, where a silver/copper (10 and 20, respectively) target is coated with a protective Rhodium layer (30), onto which a Pd target (40) has been electroplated. The plated Pd (40) is approximately of a shape to maximize the proton beam current (50) while minimizing the target material required. The proton beam is represented striking the target at a grazing angle (60) of about 1 to about 90° as measured from the surface of the target material. Preferably, the proton beam angle is of about 7°. This grazing angle allows for greater cooling efficiency of the target as the energy of the proton beam absorbed by the target face is spread over a large surface area. Furthermore, by striking the target at an angle, the target thickness also is enhanced, since the electroplated Pd layer appears thicker (by 1/sine 7°) to the beam, thereby absorbing a larger "energy bite" than that which would occur if the target was struck by the proton beam at 90°. The yield of Pd-103, the impurities of the products of the reaction, and relative cost of production can be selected and modified by varying the incident energy of the proton beam (60), varying the plated Pd thickness (40), and isotopic composition of the target material. The target material is also cooled by providing water (70) within the target support.

The target design and the quality of the applied Pd as target material is such that the target material can be irradiated with proton beam intensity of greater than 450 uA. A high quality target is important as a batch of Pd-103 may require, for example over 450 hrs (19 days) of irradiation time accumulated over a 3 to 4 week period, and the target must designed be able to withstand this exposure.

Irradiation Conditions

The energy of bombardment can be varied to optimize the yield and radionuclidic purity of the product obtained from the target material (see FIGS. 3, 4 and 5). Without wishing to limit the method of this invention in any manner, the energy for bombardment may be selected considering at least the following parameters within the bombardment process, including:

1) effective target material thickness (related to the incident angle of the proton beam and the target material thickness);

2) isotopic composition of the target material, or layering of the target material;

3) planned length of irradiation 4) average current; and 5) radionuclidic purity required in the final product.

However, other parameters may also be modified as required in order to optimize Pd-103 production.

Typically, for proton irradiation on target material comprising natural Pd, the incident energy range from about 15 to about 50 MeV would be selected. A similar incident energy range is used for deuterons. For proton irradiation of a target material enriched in Pd-104, the incident energy would be from about 15 to about 30 MeV, with a similar energy range if the irradiation source is deuteron. The current intensity of protons striking the target material is typically from about 50 to about 1000 $\mu$A, and preferably from about 100 to about 500 $\mu$A. The current, together with the length of irradiation comprises the irradiation dose, expressed in $\mu$A-hr, and can be of a few $\mu$A-hr or in the hundreds of thousands of $\mu$A-hr or more as required. It is preferred that the length of irradiation is from about 1 hour to about 1,000 hours.

The method of this invention involves continuous irradiation of the target material in order to obtain the desired level of Pd-103. However, variations on the length of irradiation or repetitions of irradiation treatments, with no separation of the product from the target material, in order to accumulate Pd-103 is also contemplated. As indicated above, the yield of product is a function—among other factors—of the irradiation dose and its associated length of time, along with the half life of the product Pd-103 (16.97 days).

One of the advantages of the method of this invention is that any unused target material may be re-exposed to proton bombardment in order to produce Pd-103 of the desired SA. Therefore, product materials comprising Pd-103, can be recycled as required following the method of this invention in order to obtain Pd-103.

Chemical Processing

Figure 6:
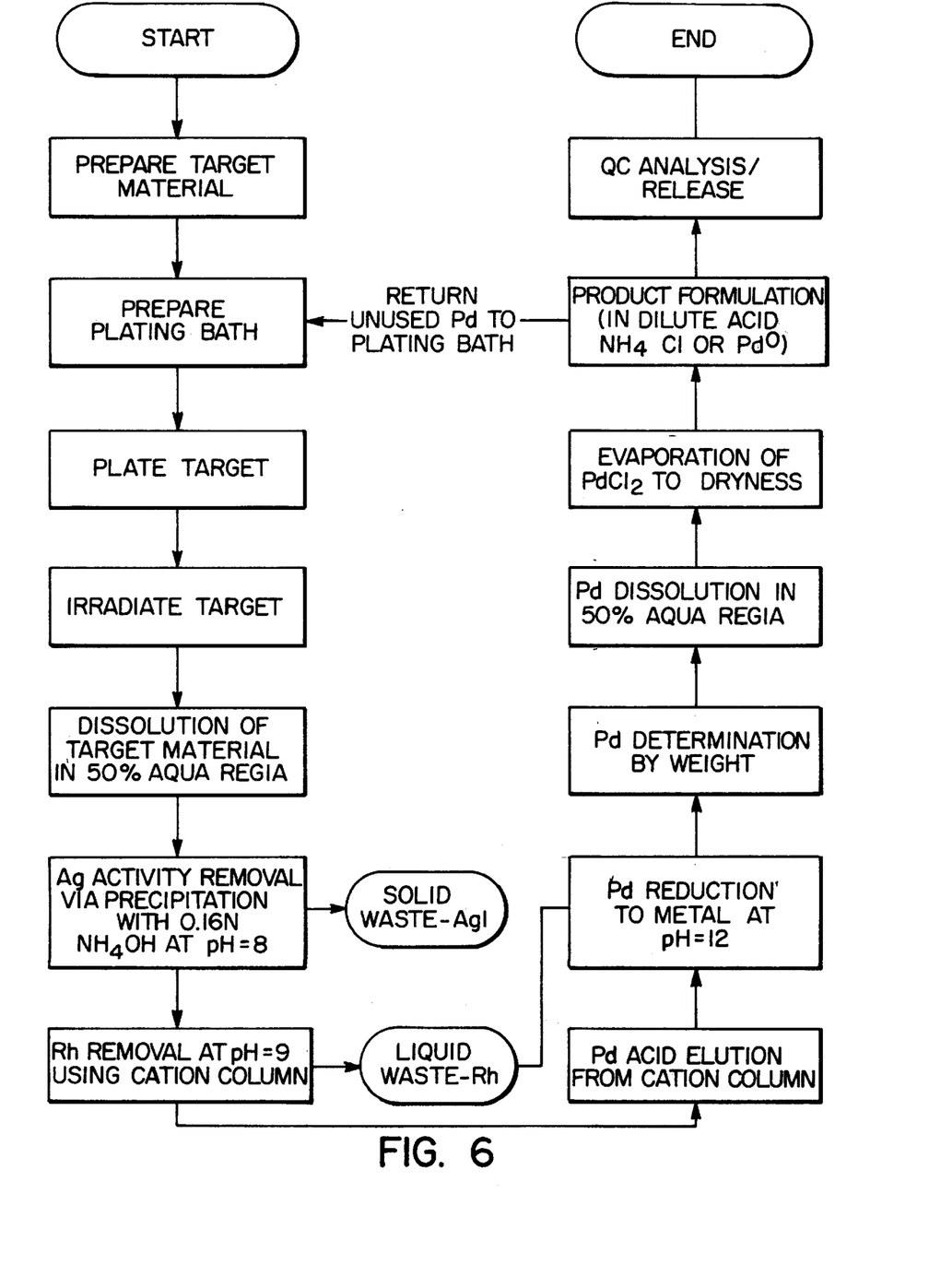
FIG. 6 shows a flow chart of the process from preparing a target through to chemically processing the irradiated target material in order to recover the product.

Following irradiation of the target, the target material is processed, typically after a specified period of time (see FIG. 6). This time period is provided in order to permit any undesired isotopes produced during the reaction (including but not limited to Pd-101, Pd-100, and Rh-101, Rh-100 products), to decay by several half lives. A suitable period of time, which is not to be considered limiting in any manner, is from about 3 to about 6 days. Following this period of time, the target material is processed in order to remove any active or inactive Ag, Rh, or a combination thereof, or any other contaminants, and obtain a suitable product formulation. This processing includes the following steps:

1) chemical processing in order to dissolve the target material from the target support and purifying the target material from radioactive and non-radioactive impurities;

2) recovering the target material and product Pd-103 into a suitable product formulation; and 3) re-using any remaining target material, if any, as a subsequent target material.

The chemical processing of the irradiated target is preferred to be performed within a few days or weeks of the end of target bombardment. Chemical processing of the irradiated target material (step 1, above) in order to recover product Pd-103 involves a series of steps including:

1) addition of suitable solvent for dissolving the Pd from the target support;

2) adding a carrier and a suitable salt to help precipitate the carrier 3) removing the carrier;

4) reducing the Pd to the metallic state; and 5) formulating into a product solution.

These steps will be outlined in more detail below, however, these detailed steps are not to be considered limiting in any manner, as substitutions for the specific solvents, carriers and salts, purification schemes ion exchange resins etc., may be modified as would be known by those skilled in the art in order to produce an isolated, purified Pd product. Reference may be made to FIG. 6 which outlines the method described below, and is to be considered a non-limiting example of a chemical processing scheme.

The removal of the target material from the target support may be carried out using any suitable container, for example a plastic tank with a seal assembly, comprising a suitable solvent that permits the target material to be dissolved from the target support. For example, and without wishing to limit this process in any manner, a mixture of HCl and $HNO_3$ may be employed for this purpose, however, other suitable solvents may also be used as known to those of skill in the art, for example mixtures of HCl and $H_2O_2$. The dissolved target material is removed and the target and tank are then rinsed with water, and the dissolved target material and rinses combined.

A small amount of a suitable carrier, for example a combination of rhodium and silver, may be added to the combined dissolved target material solution, and the solution made basic, for example with $NH_4OH$ or any other suitable base that maintains Pd in solution.

The silver carrier, and silver activities produced during irradiation of the target material are precipitated from the alkaline solution, for example in the presence of an iodide salt, as silver iodide, and the silver iodide collected as a precipitate. Other salts capable of forming complexes with, and precipitating Ag may be used for this purpose, for example which is not to be considered limiting KI, NaI, KCl, or NaCl. It is also to be understood that other methods for the purification of Pd may also be used. The precipitation step may be repeated as required until all silver activities are removed from the alkaline solution. The combined filtrates are passed over a suitable exchange column, for example, which is not to be considered limiting in any manner a cation exchange column such as Dowex AG50, in order to selectively remove the rhodium carrier. In the present example, the positively charged ammonium complex of Pd is adsorbed onto the ion exchange column, and the rhodium washed through, with for example, which is not to be considered limiting in any manner, dilute $NH_4OH$.

After sufficient rinses to remove the bulk of the rhodium activities, the column is eluted with a suitable liquid, such as warm $HNO_3$, however, other liquids may also be used, for example, which is not to be considered limiting in any manner, $H_2SO_4$ or NaOH, and the eluent made alkaline, for example with NaOH or KOH. An alcohol, for example ethanol, is then added to the solution, and the solution heated to at or near boiling in order to reduce the Pd to the metallic state. The metallic Pd is recovered by filtration and washed with water. This last step (i.e. reduction to the metal) further removes Rh contaminants from the filtrate. The Pd metal is then dried and the recovered Pd weight determined. The Pd metal is then dissolved in a solvent, for example a mixture of HCl and $HNO_3$, and taken to dryness removing excess HCl, and $HNO_3$. $PdCl_2$ is taken up into solution using dilute HCl or $NH_4OH$.

The final product, for example $PdCl_2$, is sampled, tested for pH, tested for impurities, analysed for radionuclidic purity and activity concentration, for example using a Gamma Spectrum Analysis system, and the SA calculated. Pd-103 concentrations of at least about 50 mCi/mL, with a SA of at least about 5 Ci/gm (determined at the time of purification), and a radionuclidic purity of up to 99.999% Pd-103 can be made following the method of this invention. Typically Pd-103 concentrations from about 500 to about 50,000 mCi/mL, SA of about 5 to about 500 Ci/gm (determined at the time of purification), and a radionuclidic purity up to about 99.999% Pd-103 are produced depending on the parameters of irradiation selected above (e.g. target material enrichment, beam angle, target thickness etc.), and the requirements dictated by the customer. Such product specifications are well suited for the use of Pd-103 within medical applications, and other non-medical applications should the need arise.

The resulting $PdCl_2$ salt can then be formulated into an acidic product, or a basic (e.g. ammonium) product, or both. Typical applications of Pd-103 include its use as a seed for implanting within tumours. In this application the Pd-103 is used as a coating over a carrier or base material, or mixed with a base material that is substantially non-absorbing of X-rays and that is non-reactive to the coated Pd-103. The Pd may be applied onto this base material using a variety of techniques including precipitation, deposition, electroplating etc. Suitable base materials include, but are not limited to Al, Mg, C, or polymeric materials. The coated base material may optionally be shielded with a bio-compatible material such as titanium or a polymer in order to obtain a seed useful for implanting within tumours. These seeds may also include an X-ray opaque marker such as gold, tungsten, lead or rhodium to aid their detection within the tumour following implantation. Such seeds are described with U.S. Pat. No. 3,351,049, U.S. Pat. No. 4,702,228 or U.S. Pat. No. 5,405,309 (all of which are incorporated by reference).

Pd-103 produced by the method of this invention may also be used for the coating of medical devices which may or may not be further coated with a bio-compatible material and placed within a site requiring radioactive ionization treatment. By "medical device" it is meant any apparatus that is used for the treatment of a medical ailment requiring the delivery of ionizing radiation at a site requiring such treatment. The substrate of the medical device may be metallic or non-metallic in nature. Typically the medical device is implanted, however, it may also be reversibly inserted within, and traverse the length of, an already implanted device such as a catheter (e.g. WO 93/04735, which is incorporated by reference). Furthermore, these devices may be applied on the exterior of a site requiring treatment should such a need arise. While not intended to be limiting in any manner, medical devices that may be coated using the method of this invention may include stents, expandable stents, catheters, seeds, protheses, valves, staples or other wound closure devices as would be recognized by one of skill in the art. These devices may be of arbitrary shape and for any purpose requiring the use of a radioactively treated medical device. Furthermore, it is contemplated that "medical device" also includes substrates that can be coated with a radioisotope of interest or combination thereof, and used as a radioactive source within encapsulated structures such as seeds (e.g. U.S. Pat. No. 5,163,896; U.S. Pat. No. 4,994,013; U.S. Pat. No. 4,815,449; U.S. Pat. No. 5,405,309; U.S. Pat. No. 4,702,228, which are incorporated by reference), delivery wires (e.g. U.S. Pat. No. 5,575,749) or the like as would be well known to one skilled within the art. These encapsulated structures are also considered to be medical devices.

Any Pd target material remaining after shipment of the product may be recycled for re-use.

The expiry date of Pd-103 may be selected based on the SA. For example, a Pd-103 batch with greater than 36 Ci/gm and a Pd-103 concentration of 3500 mCi/ml, would have a shelf life of over 7 weeks. Therefore, multiple large shipments of product can be provided to a customer for formulation into a desired end-product. Economics may dictate expiring the batch prior to this time, as the cost of the Pd target material shipped per mCi increases with time as the specific activity lowers due to Pd-103 decay. As the batch is expired, remaining stock is recovered for re-use as target material. As described in the purification process, the stock is made basic with NaOH, Ethanol is added, and with heating the Pd is reduced to the metal. After washing, drying and determination of weight of Pd recovered, the Pd metal is dissolved in a mixture of HCl and $HNO_3$, then the resulting solution is taken to dryness, the salt dissolved in dilute HCl, and the Pd containing HCl solution used for target material preparation, for example by electroplating.

Final product solutions of Pd manufactured by the method of this invention may be further formulated into therapeutic seeds (or other devices, or other applications) for cancer treatment. Prior art reveals that all seeds are variations of an inner seed component containing the radioactivity. These inner seed components are then encapsulated, usually in a shell, and usually a titanium shell. Permanent implants tend to have an x-ray marker within the inner seed components, while temporary implants tend to not have x-ray marker. Prior art reveals the x-ray markers may comprise a multitude of metals including Pb, Pt, Au, W, Ta, Ag, Rh, Pd, Stainless Steel, other alloys, etc. In general the x-ray marker should be biologically compatible should the seed leak, and of sufficient mass and density that it is x-ray opaque. Prior art does not reveal a Pd-103 seed prepared by a method in which the Pd-103 is applied via a technique generally known as immersion coating or displacement coating. Similarly, the prior art does not reveal a seed that is not encapsulated, or further that is sealed by wet chemical techniques. Also, the prior art does not reveal an x-ray marker that is surface modified by application of a metal layer that provides for a basis for the coating technique known as immersion coating.

It is contemplated that Pd may be directly applied to an x-ray marker by a direct reduction method known as immersion plating. This method involves x-ray markers of the appropriate size, shape and material to be contacted with an appropriate Pd/Pd-103 solution, in which the Pd and Pd-103 is quantitatively and homogeneously deposited on the outer surface of the x-ray markers by a surface reduction of the Pd by the base material itself, and/or a corresponding movement of the base metal into solution. This coating technique, by virtue of its surface reduction mechanism inherently results in a much more adherent and homogeneous layer or a much easier achievement of an adherent and homogeneous layer than that achieved by electroplating/electroless plating/etc. Experiments have shown that greater than 99% of the Pd is deposited on the substrate X-ray marker. The homogeneity is important in ensuring uniformity and reproducibility of the dosimetry of each seed. The Pd/Pd-103 may be further adhered to the x-ray marker by baking the assembly. As Pd is thought to be biologically compatible, further encapsulation of this seed assembly may not be required in order to obtaining regulatory approval. If desired, sealing of the Pd/Pd-103 coating of a seed may be accomplished by a variety of thin coating methods such as electroplating, electroless plating, or further immersion coating. Further sealing materials contemplated are those such as Rh, Pd, Au, Pt, Ag, Ni, Co, Ru.

It is also contemplated that a suitable x-ray marker for direct coating by the immersion technique may be made of metals such as Cu, or Pb due to their electrochemical properties and atomic mass/density.

A further technique may be to use Ag. Hogdahl (1961; The Radiochemistry of Palladium; Nat Acad Science, US Atomic Energy Commission) discloses the inability of Ag to reduce Pd to the metal, however it has unexpectedly been observed that the reduction may take place under some conditions. A seed insert manufacturing technique has been tested with Ag wire, however, it is to be understood that any other geometric shape of Ag could also be used (see Example 5). Following the coating protocol, inspection revealed the Pd-coated Ag rods that the Pd coating was homogeneous, coating the cut ends and length of the rod.

Seeds coated with Pd may require encapsulation for purely mechanical reasons and/or biological reasons. However an x-ray marker of a material such as those classically used may be modified such that it may be immersion coated with the Pd/Pd-103. The x-ray marker may be sufficiently alloyed with, or the surface coated by a suitable basis metal such as Ag, Cu, Pb or Al, such that they may be coated with Pd/Pd-103 by the immersion coating technique described in Example 5. The following examples are presented to further illustrate the method of this invention, however, these examples are not to be considered limiting in any manner.

EXAMPLE 1

This example demonstrates the production of Pd-103 using a natural, non-enriched Pd target material. The example highlights the process chemistry and target performance, rather than to achieve the minimum specifications required, such as specific activity, activity concentration and radionuclidic purity of the Pd-103 product. The target thickness of about 1.33 grams is designed for an irradiation energy bite of about 29 to 15 MeV.

Four grams of natural Pd is transferred to a 250 ml glass beaker and dissolved by adding a mixture of about 24 ml of one-half concentrated aqua regia (18 ml 6N HCl plus 6 ml 8N $HNO_3$). The contents are stirred and heated to about 60° C. to assist the Pd dissolution. The resulting dissolved Pd solution is taken to dryness to rid excess $HNO_3$ and HCl. The dry $PdCl_2$ salt (or $PdCl_2.xH_2O$) is dissolved in 150 ml of 0.8N HCl. This is the plating bath solution.

A silver faced target base is coated on the silver face with a thin (approx. 0.001") coating of Rh, then placed into the elliptical shaped seal of the plating cell assembly. The Pd plating solution is then warmed to between 40 and 70° C., and re-circulated through the plating cell assembly. A DC current of about 250 mA is applied to the plating assembly via a Platinum anode. The plating continues until such time as about 0.7 g of Pd is calculated to have plated onto the Rh surface. The plating is stopped, the plating cell assembly drained and the plate surface rinsed with water. After inspection and cleaning, the target is again sealed in the tank, but with the target face flipped vertically such that the prior bottom of the plate is now the top. This aids in the deposition of a homogeneous thickness of Pd. The plating operation continues until such time as the calculated deposit is about 1.33 grams The bath may be re-used until approx. 1 gram of Pd remains, or may be replenished with fresh, or recovered Pd. As the chloride content rises with usage, the bath is taken to dryness periodically to remove excess chloride. The Pd within the bath may also be recovered as the metal, and a new bath started.

The target is then irradiated with protons (using a TRI-UMF TR 30 cyclotron) at incident energy of 29 MeV, and at an incident angle to the target of about 7 degrees. The 1.33 grams of Pd in the approx. 10.2 $cm^2$ ellipse is of an appropriate thickness to absorb about 14 MeV of proton energy at this incident energy. The composition of the natural Pd is:

| | |
|---|---|
| Pd-110: | 11.8% |
| Pd-108: | 26.5% |
| Pd-106: | 27.3% |
| Pd-105: | 22.3% |
| Pd-104: | 11.1% |
| Pd-102: | 1.0% |

An irradiation at 29 to 15 MeV theoretically captures the bulk of the Pd-104 (p,2n) Ag-103/Ag-103m . . . Pd-103 and Pd-104 (p,pn) Pd-103 reactions. Additionally, a portion of the Pd-105 (p,3n) Ag-103/Ag-103m . . . Pd-103 and Pd-105 (p,p2n) Pd-103 reaction is also captured at this incident energy of 29 MeV.

The target design and the quality of the Pd electroplate is such that the target can be irradiated with proton beam intensity of greater than 450 $\mu A$. In this example, the target is irradiated for 12 hours at an average current of 350 $\mu A$.

Following irradiation, the target is allowed to decay for a period of 19 days in order to remove short lived species, and allow for radioactive impurities Pd-100 and Pd-101 to decay significantly to their daughter Rh isotopes. Pd-101 (half-life of 8.4 hrs) and Pd-100 (half-life of 3.6 days) are made exclusively from the Pd-102 component of natural Pd(1.0%) at this energy of 29 MeV. It is also possible for some Pd-101 to be made at this energy from the Rh barrier coating, with the assumption a) some proton beam misses the Pd and contacts the Rh directly at about 29 MeV and b) that a mechanism within the dissolution of the Pd target material allows some Pd-101 within the Rh to be released. After 3 days decay, the Pd-101 content would have decreased to about 0.26% of its original amount, and after 19 days decay, the Pd-100 would have decreased to about 2.6% of its original amount.

The target is dissolved by assembling a plastic tank onto the target face with a rubber seal, heating the target face to between about 50 and 80° C., and adding a 12 mL mixture of 50% aqua regia to the tank. After about 30 minutes, the Pd target material is dissolved completely, as indicated by the observation of a clean Rh surface. The dissolved target material solution is transferred to a 100 mL glass beaker, then the target face and tank walls are rinsed with 2 by 10 mL $H_2O$, and these rinses added to the beaker. Radiation fields from the target support and beaker are taken as indicators of the dissolution process.

To begin the separation chemistry of Ag and Rh, 50 mg of Ag as $AgNO_3$ in solution and 10 mg of Rh as $Rh(NO_3)_3.xH_2O$ in solution are added to the 100 mL beaker contents. For a minimum of about 20 minutes, the solution is then stirred and heated to between about 50 and 80° C. to promote exchange of the radioactive Ag and Rh with the inactive carrier. To prepare for the separation of Ag, the solution is then made basic to about pH 9 to 10 by the addition of 2 by 5 mL of conc. $NH_4OH$. A red/brown Pd/amine precipitate will first form, then dissolve to form a clear yellow basic solution.

Two mL of a 5% solution of potassium iodide is added, precipitating AgI. The yellow AgI precipitate is further enhanced by stirring and boiling the solution, coagulating the precipitate. This heating also lowers the pH closer to neutral as excess NH$_4$OH is expelled from the solution. This lower pH increases the insolubility of the AgI. After boiling for about 5 minutes, the solution is allowed to cool to near room temperature to further enhance the AgI insolubility. The solution is then filtered to remove the AgI. This entire AgI precipitation step can be repeated.

The removal of Rh is performed via cation exchange. A 1.5 by 10 cm bed of AG50WX8 resin is prepared in a glass column, then conditioned with 10% NH$_4$OH (approximately 0.1 6N). The filtrate from the AgI separation is pumped onto the column using a peristaltic pump. The Pd as Pd(NH$_3$)$_4^{2+}$ is adsorbed at or near the top half of the resin bed. The Rh is not strongly adsorbed on the column in the dilute NH$_4$OH matrix of the AgI filtrate, and passes through to the effluent. The filtrate solution holder and column are then farther washed with 2 by 20 mL H$_2$O. The resin bed is then washed with 240 mL of 10% NH$_4$OH to continue washing Rh from the column. The column is then further washed with 60 mL H$_2$O.

To elute the Pd from the column, 60 mL of warm, 40 to 70° C. 8N HNO$_3$ is pumped through the column, eluting the Pd into a 250 mL glass beaker. The column is then further rinsed with 2 by 10 mL H$_2$O to the beaker. The Pd is then reduced to the metal prior to final product formulation. This reduction allows for a) further Rh removal, b) the removal of salts, and c) a determination by weight of the recovered Pd mass.

To reduce the Pd to the metal, 60 mL of 10N NaOH is slowly added to increase the pH to about 12. Fifteen mL of ethanol is then added. The solution is stirred, and heated to 80 to 100° C. The Pd metal begins to come out of solution within about 10 min, as indicated by the darkening of the solution, the formation of a Pd metal layer on the beaker walls, and an accumulation on the beaker bottom. The solution is boiled for 10 min to ensure complete Pd reduction, then allowed to cool and settle for about 10 minutes. The supernatant is removed from the Pd via suction threw a frit. The Pd metal, beaker, and frit are then washed with 6 by 20 mL H$_2$O. The Pd metal is then dried at about 150° C., cooled to room temperature, weighed, and the percentage of Pd recovery determined. The percent recovered is greater than 95%.

To formulate the product solution, the Pd metal is first dissolved in 8 mL of ½ concentrated aqua regia, plus heat of about 60° C. The dissolved Pd is then taken to dryness at about 150° C. This action will rid the excess HNO$_3$ and HCl, leaving a dry salt of approximate composition PdCl$_2$.xH$_2$O. The contents are then cooled to room temperature.

The final product is made up in pH 8 to 10 dilute NH$_4$OH. Ten mL of H$_2$O, then 5 mL of concentrated NH$_4$OH is added to the beaker, and the contents stirred and heated at about 90° C. A thick red/brown precipitate forms, then slowly dissolves to form a clear yellow solution. When all the precipitate has dissolved, the solution is boiled for about 2 minutes to expel excess NH$_4$OH, lowering the pH to about neutral. The solution is then cooled to room temperature, and 1 mL of 10% NH$_4$OH added to raise the pH to between 8 and 10. The Pd is now an amine complex in the form of Pd(NH$_3$)$_{2\,or\,4}$Cl$_2$. This complex is soluble in dilute NH$_4$OH such that at least 80 to 100 mg Pd is soluble per mL of solution. If required, H$_2$O is added to dilute the Pd concentration to this range.

The above solution is filtered via a 20 mL syringe and 0.22$\mu$ filter to a 30 mL glass product vial. The beaker, syringe and filter are rinsed with 2×2 mL H$_2$O, and the rinses added to the product vial. The final volume of the product solution is measured. In this example, the volume should be such that the Pd concentration is 60 to 70 mg/mL. H$_2$O is added to adjust the final Pd concentration. When the final volume is correct, then a small sample is taken for analysis.

For this 12 hour, 29 MeV proton irradiation on 1.33 grams of natural Pd, a dose of 4,200 $\mu$Amp-hours is achieved with an average current of 350 $\mu$A. The amount of Pd-103 produced at 20 days post irradiation, assuming a 95% Pd recovery and 90% utilisation of the 350 $\mu$A beam is about 450 mCi +/−10%. The radionuclidic purity is from about 99.80 to about 99.95% Pd-103.

EXAMPLE 2

This example utilizes a 33% enriched Pd-104 target material. The example highlights the achievement of a useful final product with regards to Pd-103 concentration, Pd concentration, specific activity, and radionuclidic purity. The target thickness of about 0.73 grams is designed for an irradiation energy bite of about 27 to 19 MeV.

Three grams of natural Pd and one gram of >95% enriched Pd-104 are transferred to a 250 mL glass beaker and dissolved by adding a mixture of about 24 ML of one-half concentrated aqua regia (18 mL 6N HCl plus 6 mL 8N HNO$_3$). The contents are stirred and heated to about 60° C. to assist the Pd dissolution. The resulting dissolved Pd solution is taken to dryness to rid excess HNO$_3$. The dry PdCl$_2$ salt (or PdCl$_2$.xH$_2$O) is dissolved in 150 mL of 0.8N HCl. This is the plating bath solution.

A silver faced target base is coated on the silver face with a thin (approx. 0.001") coating of Rh, then placed into the elliptical shaped seal of the plating cell assembly. The Pd plating solution is then warmed to between 40 and 70° C., and re-circulated through the plating cell assembly. A DC current of about 250 mA is applied to the plating assembly via a Platinum anode. The plating continues until such time as about 0.35 g of Pd is calculated to have plated onto the Rh surface. The plating is stopped, the plating cell assembly drained and the plate surface rinsed with water. After inspection and cleaning, the target is again sealed in the tank, but with the target face flipped vertically such that the prior bottom of the plate is now the top. This aids in the deposition of a homogeneous thickness of Pd. The plating operation continues until such time as the calculated deposit is about 0.73 grams.

The bath may be re-used until approx. 1 gram of Pd remains, or may be replenished with fresh, or recovered, Pd. As the chloride content rises with usage, the bath is taken to dryness periodically to remove excess chloride. The Pd within the bath may also be recovered as the metal, and a new bath started.

The target is then irradiated with protons at incident energy of 27 MeV, and at an incident angle to the target of about 7 degrees. The incident energy of 27 MeV is chosen to maximise the Pd-103 yield for the 0.73 grams Pd, while discriminating against the production of Pd-100. This 0.73 grams of Pd in the approx. 10.2 cm$^2$ ellipse is of an appropriate thickness to absorb about 8 MeV of proton energy at this incident energy. This blend of 3 grams natural to 1 gram highly enriched Pd-104 produces a composition as follows:

| | |
|---|---|
| Pd-110: | 8.9% |
| Pd-108: | 19.9% |
| Pd-106: | 20.6% |
| Pd-105: | 17.1% |
| Pd-104: | 32.8% |
| Pd-102: | 0.8% |

An irradiation at 27 to 19 MeV is expected to capture most of the Pd-104 (p,2n) Ag-103/Ag-103m . . . Pd-103 and Pd-104 (p,pn) Pd-103 reactions. Additionally, a small portion of the Pd-105 (p,3n) Ag-103/Ag-103m . . . Pd-103 and Pd-105 (p,p2n) Pd-103 reaction is also captured at this incident energy of 29 MeV.

The target design and the quality of the Pd electroplate is such that the target can be irradiated with proton beam intensity of greater than 450 $\mu$A. In this example, the target is irradiated for a total of 340 hours at an average current of 390 $\mu$A. The irradiation dose of 132,600 $\mu$Ahr is accumulated via multiple short irradiations spread five week period.

In this example, the target is allowed to decay after irradiation for a period of 4 days. After 4 days decay, the Pd-101 content decreases to about 0.04% of its original amount, and after 4 days decay, the Pd-100 decreases to about 46% of its original amount.

The product material is purified as outlined in Example 1.

Following the step of filtering via a 20 mL syringe fitted with a 0.22$\mu$ filter, the beaker, syringe and filter are rinsed with 2×2 mL H2O, and the rinses added to the product vial. The final volume of the product solution is measured. In this example, the volume should be such that the Pd concentration is 40 to 70 mg/mL, and the Pd-103 concentration is 750 to 1500 mCi/mL, and the specific activity is 16 to 35 Ci/gram. $H_2O$ is added to adjust the final Pd and Pd-103 concentration.

For this 340 hour, 27 MeV proton irradiation on 0.73 grams of 33% enriched Pd, a dose of 132,600 $\mu$Amp-hours is achieved via short irradiations accumulated over a five week period. The average currents during the irradiations are 390 $\mu$A. The amount of Pd-103 produced at 10 days post irradiation, assuming a 95% Pd recovery and 90% utilisation of the 390 $\mu$A beam is about 21,600 mCi +/−10%. The radionuclidic purity is from about 99.91 to about 99.98% Pd-103. The specific activity is about 30 Ci Pd-103/gram Pd +/−10%.

EXAMPLE 3

This example utilizes a >95% enriched Pd-104 target material. The example highlights the achievement of a large batch size of useful final product with regards to Pd-103 concentration, Pd concentration, specific activity, and radionuclidic purity. The target thickness of about 1.26 grams is designed for an irradiation energy bite of about 29 to 16 MeV.

Four grams of >95% enriched Pd-104 are transferred to a 250 mL glass beaker and dissolved by adding a mixture of about 24 mL of one-half concentrated aqua regia (18 mL 6N HCl plus 6 mL 8N $HNO_3$). The contents are stirred and heated to about 60° C. to assist the Pd dissolution. The resulting dissolved Pd solution is taken to dryness to rid excess $HNO_3$. The dry $PdCl_2$ salt (or $PdCl_2.xH_2O$) is dissolved in 150 mL of 0.8N HCl. This is the plating bath solution.

A silver faced target base is coated on the silver face with a thin (approx. 0.001") coating of Rh, then placed into the elliptical shaped seal of the plating cell assembly. The Pd plating solution is then warmed to between 40 and 70° C., and re-circulated through the plating cell assembly. A DC current of about 250 mA is applied to the plating assembly via a Platinum anode. The plating continues until such time as about 0.65 g of Pd is calculated to have plated onto the Rh surface. The plating is stopped, the plating cell assembly drained and the plate surface rinsed with water. After inspection and cleaning, the target is again sealed in the tank, but with the target face flipped vertically such that the prior bottom of the plate is now the top. This aids in the deposition of a homogeneous thickness of Pd. The plating operation continues until such time as the calculated deposit is about 1.26 grams.

The bath may be re-used until approx. 1 gram of Pd remains, or may be replenished with fresh, or recovered, Pd. As the chloride content rises with usage, the bath is taken to dryness periodically to remove excess chloride. The Pd within the bath may also be recovered, and a new bath started.

The target is then irradiated with protons at incident energy of 29 MeV, and at an incident angle to the target of about 7 degrees. The incident energy of 29 MeV is chosen to maximise the Pd-103 yield for the 1.26 grams Pd. This 1.26 grams of Pd in the approx. 10.2 $cm^2$ ellipse is of an appropriate thickness to absorb about 13 MeV of proton energy at this incident energy. This highly enriched Pd-104 has an approximate composition as follows:

| | |
|---|---|
| Pd-110: | 0.2% |
| Pd-108: | 0.8% |
| Pd-106: | 1.5% |
| Pd-105: | 2.5% |
| Pd-104: | 95% |
| Pd-102: | .05% |

An irradiation at 29 to 16 MeV captures almost all of the Pd-104 (p,2n) Ag-103/Ag-103m . . . Pd-103 and Pd-104 (p,pn) Pd-103 reactions.

The target design and the quality of the Pd electroplate is such that the target can be irradiated with proton beam intensity of greater than 450 $\mu$A. In this example, the target is irradiated for a total of 270 hours at an average current of 500 $\mu$A. The irradiation dose of 135,000 $\mu$Ahr is accumulated via irradiations spread over a 2 week period.

In this example, the target is allowed to decay after irradiation for a period of 3 days. This mainly allows the radiation field from the target to drop dramatically as short lived species decay. Additionally this allows for Pd-101 and Pd-100 to decay significantly to their daughter Rh isotopes. Pd-101 (half-life of 8.4 hrs) and Pd-100 (half-life of 3.6 days) are made exclusively from the Pd-102 component of natural Pd (1.0%) at this energy of 29 MeV. However, there is very little Pd-102 remaining in the highly enriched Pd-104 target material (approx. 0.05%), so these impurities Pd-101 and Pd-100 are only made in very small quantity, and the product Pd-103 produced from highly enriched Pd-104 would have high radionuclidic purity. It is also possible for some Pd-101 to be made at this energy from the Rh barrier coating, with the assumption a) some proton beam misses the Pd and contacts the Rh directly at about 29 MeV and b) that a mechanism within the dissolution of the Pd target material allows some Pd-101 within the Rh to be released. After 3 days decay, any Pd-101 would have decreased to about 0.26% of its original value, and after 3 days decay, the Pd-100 would have decreased to about 56% of its original amount.

The target is dissolved, and the product Pd-103 purified as described in Example 1.

To formulate the product solution, the Pd metal is first dissolved in 8 mL of ½ concentrated aqua regia, plus heat of about 60° C. The dissolved Pd is then taken to dryness at about 150° C. This action will rid the excess $HNO_3$ and HCl, leaving a dry salt of approximate composition $PdCl_2 \cdot xH_2O$. The contents are then cooled to room temperature.

In this example, the final product is to be in dilute 0.8N HCl. Eighteen mL of 0.8N HCl is added to the dry salt, and the contents stirred and heated at about 60° C. A dark red/brown solution is formed as the $PdCl_2 \cdot xH_2O$ slowly dissolves. When all the $PdCl_2 \cdot xH_2O$ has dissolved, the solution is transferred to a 30 mL glass vial. The beaker is rinsed with 3 by 3 mL of 0.8N HCl. The rinses are added to the glass vial.

The rough product solution is then filtered via a 20 mL syringe and $0.22\mu$ filter to a second 30 mL glass product vial. The first glass vial, syringe and filter are rinsed with 2×2.5 mL 0.8N HCl, and the rinses added to the product vial. The final volume of the product solution is measured. In this example, the Pd concentration is 30 to 60 mg/mL, and the Pd-103 concentration is 3,000 to 5,000 mCi/mL, and the specific activity is 70 to 120 Ci/gram. 0.8N HCl is added to adjust the final Pd and Pd-103 concentration. When the final volume is correct, then a small sample is taken for analysis.

For this 270 hour, 29 MeV proton irradiation on 1.26 grams of >95% enriched Pd-104, a dose of 135,000 $\mu$Amp-hours is accumulated over a two week period. The average current during the irradiations is 500 $\mu$A. The amount of Pd-103 produced at 7 days post irradiation, assuming a 95% Pd recovery and 100% utilisation of the 500 $\mu$A beam is about 122,000 mCi $^{+/-}$20%. The radionuclidic purity is from about 99.98 to about 99.99% Pd-103. The specific activity is about 96 Ci Pd-103/gram Pd $^{+/-}$20%.

EXAMPLE 4

Pd may be directly applied to a substrate material such as an x-ray marker by a direct reduction method known as immersion plating. This method involves x-ray markers of the appropriate size, shape and material, preferably Ag, to be contacted with an appropriate Pd/Pd-103 solution, in which the Pd and Pd-103 is quantitatively and homogeneously deposited on the outer surface of the x-ray markers by a surface reduction of the Pd by the base material itself, and/or a corresponding movement of the base metal into solution. This coating technique, by virtue of its surface reduction mechanism inherently results in a much more adherent and homogeneous layer or a much easier achievement of an adherent and homogeneous layer than that achieved by electroplating/electroless plating/etc. The homogeneity is important in ensuring uniformity and reproducibility of the dosimetry of each seed. The Pd/Pd-103 may be further adhered to the substrate material (including x-ray marker) by baking the assembly. If desired, sealing of the Pd/Pd-103 coating of a seed may be accomplished by a variety of thin coating methods such as electroplating, electroless plating, or further immersion coating. Further sealing materials contemplated are those such as Rh, Pd, Au, Pt, Ag, Ni, Co, Ru.

Hogdahl (1961; The Radiochemistry of Palladium; Nat Acad Science, US Atomic Energy Commission) discloses the inability of Ag to reduce Pd to the metal, however it has unexpectedly been observed that the reduction may take place under some conditions. A seed insert manufacturing technique has been tested with Ag wire of the appropriate size and shape.

To immersion coat a Ag substrate with Pd, a "blank" dilute 0.8N HCl (however, other concentration of HCl are also contemplated, for example 0.1 to 1.0 N HCl) Pd stock solution (ie not active) where the Pd concentration was 60 mg/mL is prepared. Assuming an active solution to also contain about 1000 mCi/mL of Pd-103, and that each seed insert required 5 mCi of activity, then 200 seeds would require the deposition of 1000 mCi or the Pd content of 1 mL of the solution or 60 mg. Pure silver wire of 0.5 mm diameter and 1 meter length is cleaned, and cut into 200 rods of 5 mm length each. One mL of the Pd blank solution is placed in a glass vial, a Teflon stir bar added, and the solution diluted to about 20 mL with $H_2O$. This diluted solution remains intensely coloured even at this more diluted Pd concentration. The 200 silver rods are added to the vial, the mixture stirred, and heated to 70 to 90° C. The silver rods are slowly coated with the darker Pd, and after 30 min, the solution was colourless, the vial walls and stir bar clean, indicating complete deposition onto the Ag rods. Only the Ag rods were observed to be coated, with greater than 99% of the Pd plated onto the substrate. The solution is drained from the rods, the rods washed with $H_2O$, and dried in the vial at about 110° C. After cooling, visual inspection revealed the rods had no Ag spots showing, and that the Pd appeared homogeneous, also coating the cut ends.

Solutions of higher activity concentration, and/or of lower inactive Pd concentration, and/or seeds to be coated with less activity each would be feasible using the above technique. The technique can deposit at least 60 mg of Pd (active or nonactive or a combination of) on 200 Ag rods of the described size and shape. It is assumed that approx. a chemically equivalent amount of Ag (about 121 mg) dissolves from the rods into solution—although no AgCl precipitate was observed.

The present invention has been described with regard to preferred embodiments. However, it will be obvious to persons skilled in the art that a number of variations and modifications can be made without departing from the scope of the invention as described herein.

The embodiments of the invention in which an exclusive property of privilege is claimed are defined as follows:

1. A method for the production of Pd-103 comprising;
   i) providing a target material enriched with Pd isotopes comprising atomic masses equal to or greater than Pd-103;
   ii) applying the target material onto a target support;
   iii) irradiating the target material with protons or deuterons of sufficient incident energy and time to convert at least some of the Pd isotopes within the target material to Pd-103; and
   iv) purifying Pd from the non-Pd components.

2. The method of claim 1 wherein the target material is enriched with Pd-104, Pd-105, Pd-106, or a combination thereof.

3. The method of claim 2 wherein the target material is enriched with Pd-104.

4. The method of claim 3 wherein the target material is a foil, or the target material is applied to the target support using electroplating, deposition, or precipitation.

5. The method of claim 4 wherein the target material is applied using electroplating.

6. The method of claim 4 wherein the target material is formed by layering Pd isotope-containing target materials so that each layer is enriched with Pd isotopes comprised of predominantly different atomic mass.

7. The method of claim 1 wherein the target support is protected by a coating comprising a barrier layer.

8. The method of claim 7, wherein the barrier layer is comprised of rhodium.

9. The method of claim 8, wherein the incident energy of said protons or deuterons is greater than about 10 MeV.

10. The method of claim 9 wherein the protons or deuterons are provided as a beam angled from about 1 to about 90° as measured from the surface of the target material.

11. The method of claim 10, wherein the target material is of a shape that is similar to the shape of the proton beam that strikes the surface of the target material.

12. The method of claim 11, wherein the incident energy of the protons is from about 23 to about 30 MeV, and the angle of the proton beam is about 7° as measured from the surface of the target material.

13. The method of claim 12, wherein the target material is irradiated with protons or deuterons from about 1 hour to about 1,000 hours.

14. The method of claim 1, wherein the specific activity of the Pd-103 is greater than about 5 Ci/gm.

15. The method of claim 1, wherein the Pd-103 is reused as the target material.

16. The method of claim 1 wherein the step of purifying Pd-103 comprises:
   i) adding a solvent to remove the target material from the target support to produce a target material solution;
   ii) adding at least one carrier;
   iii) removing the at least one carrier from the target material solution; and
   iv) reducing the Pd to the metallic state.

17. The method of claim 16 wherein the step of removing the at least one carrier from the Pd, adsorbs and selectively removes impurities produced during the production of Pd-103.

18. The method of claim 17, wherein the carrier is silver, and an iodide salt is added to selectively remove silver.

19. The method of claim 17, wherein the carrier is rhodium, and it is removed from the Pd precipitate using an ion-exchange resin.

20. The method of claim 19, wherein rhodium is further removed from Pd-103 during reduction of Pd to the metallic state.

21. A method of coating a silver device by emersion plating comprising, immersing the silver device in an acidified Pd solution, heating the Pd solution containing the silver device to produce a Pd-coated device, removing the Pd solution; and drying the Pd-coated device.

22. The method of claim 21 wherein the Pd solution is a 0.1 to 1.0 N HCl Pd solution.

23. A Pd-coated silver device produced by the method of claim 21.

24. The Pd-coated silver device of claim 23, wherein the Pd-coated silver device can comprise a variety of surface geometries, and is selected from the group consisting of: stent, expandable stent, catheter, seed, protheses, valves, and staples or other wound closure device.

* * * * *